United States Patent [19]

van Holten et al.

[11] 3,981,926

[45] Sept. 21, 1976

[54] PURIFICATION OF SOLID ORGANIC PEROXIDES

[75] Inventors: Jan van Holten, Zwijndrecht; Cornelis Ribbens, Dordrecht, both of Netherlands

[73] Assignee: N.V. Chefaro Maatschappij, Rotterdam, Netherlands

[22] Filed: Mar. 3, 1969

[21] Appl. No.: 803,841

[30] Foreign Application Priority Data

Mar. 4, 1968 Netherlands...................... 6803015

[52] U.S. Cl............................ 260/610 D; 260/610 A
[51] Int. Cl.[2]....................................... C07C 179/14
[58] Field of Search..................... 260/610 A, 610 D

[56] References Cited
UNITED STATES PATENTS

| | | | |
|---|---|---|---|
| 2,906,789 | 9/1959 | McNaughtan | 260/610 A |
| 3,367,951 | 2/1968 | Nielsen et al. | 260/610 A |

FOREIGN PATENTS OR APPLICATIONS

| | | | |
|---|---|---|---|
| 950,978 | 3/1964 | United Kingdom | 260/610 D |

Primary Examiner—James O. Thomas, Jr.
Assistant Examiner—W. B. Lone
Attorney, Agent, or Firm—Alvin Sinderbrand

[57] ABSTRACT

In purifying a normally solid organic peroxide by heating an aqueous suspension of the organic peroxide in an impure state to a temperature above the melting point of the peroxide for converting the suspension to an aqueous emulsion and then separating the resulting aqueous and liquid peroxide phases so that the separated peroxide phase can be solidified by cooling; the heating of the aqueous suspension is effected by injecting finely divided steam therein during its continuous transport in one or more paths leading to the separator for obtaining complete melting immediately prior to entry of the emulsion into the separator without substantial decomposition of the organic peroxide.

5 Claims, 1 Drawing Figure

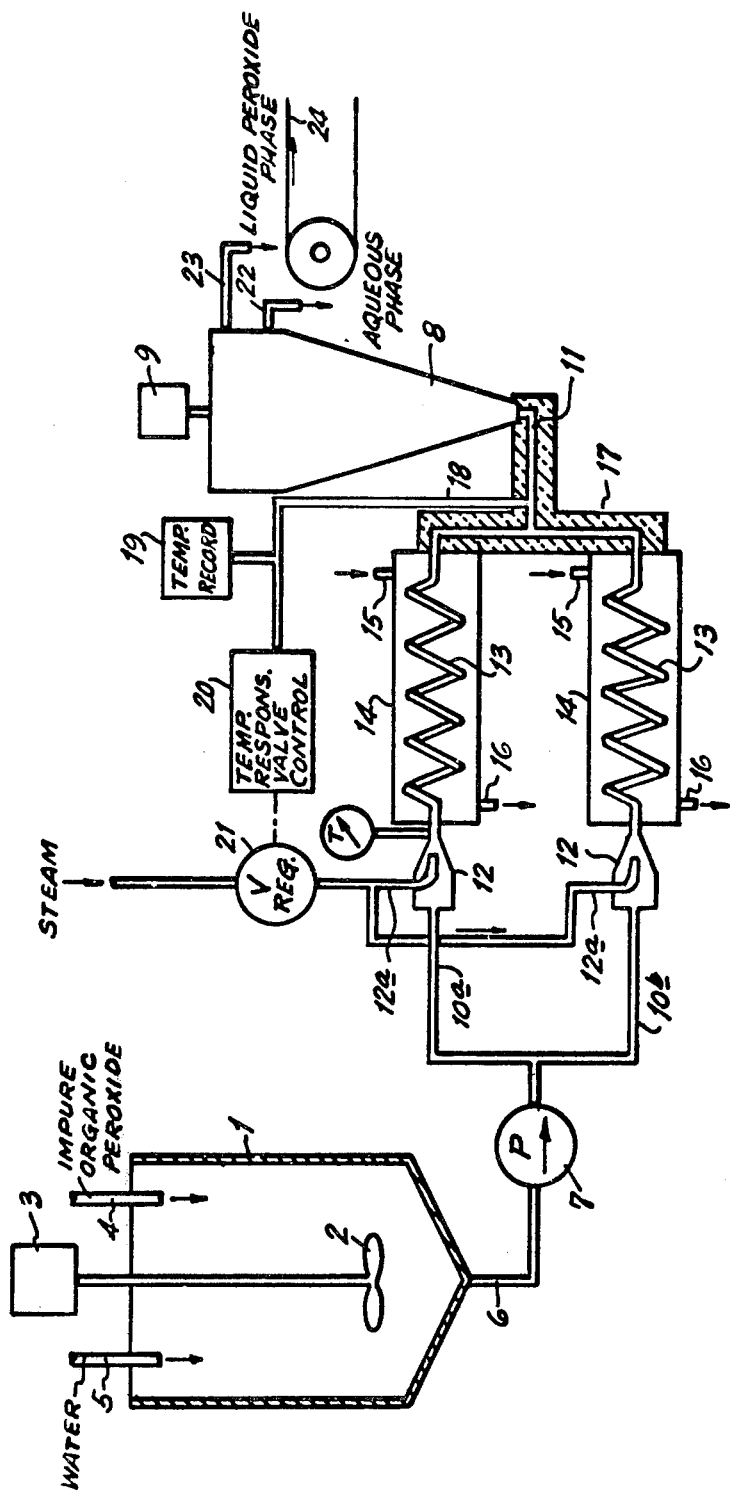

PURIFICATION OF SOLID ORGANIC PEROXIDES

This invention relates generally to a method and apparatus for the purification of organic peroxides, particularly aliphatic diacyl peroxides, which are normally solid and fuse or melt at temperatures below 120°C.

It is known that aliphatic diacyl peroxides, when heated to temperatures above their melting points, are not stable particularly when in contact with alkaline aqueous liquids. Thus, in Houben-Weyl 1952 (Vol. VIII), Page 40, at line 25, it is suggested that in producing aliphatic diacyl peroxides by reacting the corresponding acid chlorides with sodium peroxide or hydrogen peroxide and lye in an aqueous medium, the reaction should be performed at low temperatures in the range betwen −5° and −10°C. However, at these low temperatures, the reaction proceeds slowly and requires approximately 1 hour for its completion. In order to reduce such long reaction time to between 30 seconds and 5 minutes, it has been suggested, for example, in the Netherlands patent application Ser. No. 270,329, which has been laid open to public inspection, to effect the described reaction at temperatures between 50° and 60°C., provided that, at the conclusion of the shortened reaction time, the reaction mixture is rapidly cooled to room temperature so as to limit the time during which the formed peroxide is held at elevated temperatures and thereby substantially avoid decomposition of the diacyl peroxide.

However, whether the diacyl peroxide is produced at low or elevated temperatures, as described above, the diacyl peroxide thereby obtained is not sufficiently pure for many purposes. Thus, the reaction product may contain unreacted acid chloride and free fatty acid and/or alkali salts which have formed as by-products of the peroxide formation reaction or which were present, as impurities, in the acid chloride reactant. Therefore, it is usually necessary to subject the reaction product to a purifying treatment which generally consists of intensive washing thereof with water, diluted lye or other aqueous solutions. Such washing of the crystallized form of aliphatic diacyl peroxide is very time-consuming as the unreacted acid chloride reacts only slowly with water at the low washing temperatures that are generally employed. Furthermore, the impurities occluded in the crystal agglomerates are removed by the washing procedure only with considerable difficulty, if at all.

It is apparent that the purification would proceed very much more rapidly and completely if performed at temperatures above the melting point of the formed organic peroxide. At such elevated temperatures, the decomposition of unreacted acid chloride is greatly accelerated, the solubility of various impurities in the water is increased, and there is more intimate contact between the aqueous phase and the liquid peroxide phase that result so that the washing is more effective. However, the duration of such contact of the aqueous and liquid peroxide phases must be limited, as otherwise substantial decomposition of the peroxide will result.

In view of the foregoing, various arrangements have been proposed for effecting the purification of the formed organic peroxide at elevated temperatures. For example, in Netherlands patent application Ser. No. 6,611,234, a suspension in water of the organic peroxide in an impure state is pumped into a vessel or container provided with a stirrer and in which heated water, at a temperature between 80° and 90°C., is mixed with the suspension to convert the latter to an emulsion. Such emulsion is drained from the mixing vessel or container through a sieve in the bottom of the latter and conducted to a separator in which the aqueous and liquid peroxide phases of the emulsion are separated, whereupon the separated liquid peroxide phase is cooled to solidify the purified peroxide. Although it is stated that, in the described arrangement, the time during which the emulsion resides in the vessel or container where the suspension is mixed with heated water is limited to avoid decomposition of the peroxide, as a practical matter, that limitation cannot be realized with respect to all of the peroxide. More specifically, by reason of the substantial volume of the aqueous suspension of organic peroxide being mixed with hot water in the mixing vessel, the times during which all portions of the peroxide are at elevated temperatures to achieve melting of all of the peroxide cannot be made uniform and at least some of the peroxide is held at the elevated temperature for more than the desired time so that at least some decomposition of the peroxide cannot be avoided.

Another arrangement for purifying normally solid organic peroxides at elevated temperatures is disclosed in U.S. Pat. No. 3,367,951, in which the suspension of the impure organic peroxide in water is pumped through the coiled pipe of a heat exchanger having a jacket to which hot water is supplied for melting the peroxide as it travels through the coiled pipe, the resulting emulsion is fed from the heat exchanger to a centrifugal separator where the aqueous and liquid peroxide phases are separated, and the separated liquid peroxide is solidified by cooling. In this arrangement, the heating of the suspension occurs by heat transfer through the wall of the coiled pipe in the heat exchanger, from which it follows that, in order to heat the peroxide at the center of the pipe to its melting temperature, the portions of the peroxide adjacent the wall surface of the pipe will have to be heated to or above the melting point for a relatively longer period of time and thus subject to decomposition by reason of the extended heating.

Accordingly, it is an object of this invention to provide a method and apparatus by which normally solid organic peroxides, such as aliphatic diacyl peroxides, may be efficiently purified while avoiding any significant decomposition of the peroxide.

Another object is to effect the purification at an elevated temperature above the melting point of the organic peroxide, but in which the heating to such elevated temperature is conducted in a manner to avoid decomposition of the peroxide.

According to an aspect of this invention, in the purification of a normally solid organic peroxide by heating an aqueous suspension of the organic peroxide in an impure state to a temperature above the melting point of the peroxide for converting the suspension to an aqueous emulsion and then separating the resulting aqueous and liquid peroxide phases so that the separated peroxide phase can be solidified by rapid cooling, the heating of the aqueous suspension is effected by injecting finely divided steam therein during its continuous transport in one or more paths leading to the separator.

The temperature of the steam injected into the aqueous suspension of organic peroxide in each path along which the latter is continuously transported to the separator, which is preferably of the centrifugal type, the rate of injection of the steam, the rate at which the suspension is transported in each such path, and the distance along the path from the point of injection of the steam to the separator are selected so that the suspension is gradually heated, as a whole, to a temperature just above the melting point of the peroxide and thereby converted to an emulsion during its transport from the point of steam injection, with the suspension being fully converted to an emlusion, that is, all of the normally solid organic peroxide being melted or fused, immediately prior to the discharge of the emulsion into the centrifugal separator.

It has been found that, when heating of the suspension of organic peroxide is thus effected according to the invention by directly injecting steam into one or more continuous flows of the suspension, the direct and intimate contact of the steam with the suspension results in a very rapid and uniform transfer of heat to the suspension to achieve full conversion to the emulsion with all portions of the organic peroxide being subjected to a temperature above the melting point for uniform short periods of time. By reason of the extremely short, uniform periods of time during which heating is effected for melting the organic peroxide, the total contact time of the aqueous and liquid peroxide phases at temperatures above the melting point of the peroxide, that is, the time from injection of steam for melting the peroxide to the separation of the liquid peroxide phase from the aqueous phase and its rapid cooling, can be made so short, for example, no more than 2 minutes, as to avoid any significant decomposition of the peroxide, while the purification of the peroxide is achieved to a hitherto unattainable degree. For example, when aliphatic diacyl peroxides, which are normally solid and have melting points lower than 120°C., are purified in accordance with this invention, degrees of purity in excess of 99% can be achieved with substantially no decomposition. Using conventional washing methods, as initially described herein, corresponding degrees of purity are generally not achieved or, if achieved, are attained only at the expense of much time and work. Furthermore, as regards the fatty acid content, a degree of purity in excess of 99%, as achieved according to this invention, constitutes a very substantial improvement over all previous purifying treatments.

The process and apparatus according to this invention will now be described in greater detail with reference to the accompanying drawing in which the single view is a schematic representation of an apparatus according to an illustrative embodiment.

As shown on the drawing an apparatus for purifying an organic peroxide, for example, the reaction product obtained in the conventional process for obtaining aliphatic diacyl peroxides, such as dilauroyl peroxide, dicapryloyl peroxide or the like, may comprise a mixing vessel or container 1 provided with a stirrer or agitator 2 driven by a motor 3 and to which the above mentioned reaction product and water are continuously supplied, as at 4 and 5, respectively, in suitably proportional rates. The water supplied to vessel 1 may be at room temperature or at an elevated temperature well below the melting point of the organic peroxide.

The water and reaction product containing the organic peroxide to be purified are mixed in vessel 1 by agitator 2 to provide an aqueous suspension which is continuously withdrawn from vessel 1 through a conduit 6 having a pump 7 interposed therein and is continuously transported by the latter in at least one path, and preferably in a plurality of parallel paths, as shown, leading to the inlet of a suitably heated centrifugal separator 8 driven by a motor 9. The plural paths for the suspension propelled by pump 7 are shown to be constituted by tubes or conduits 10a and 10b branching from conduit 6 and then merging in a short conduit 11 extending to the inlet of separator 8.

In accordance with this invention, each of tubes or conduits 10a and 10b has a steam injector 12 interposed therein which receives steam, as at 12a, and is operative to inject such steam in finely divided form into the flow of suspension in the respective conduit 10a or 10b. Thus, the injected steam is uniformly and directly contacted with the suspension flowing in each conduit 10a or 10b for rapid and uniform heat transfer to the suspension. Heat loss to the atmosphere is preferably avoided along the portions of conduits 10a and 10b extending downstream from injectors 12 and along conduit 11. For example, as shown, the major portion of the length of each of conduits 10a and 10b extending downstream from injector 12 may be coiled, as at 13, within a jacket 14 having an inlet 15 and outlet 16 for the circulation of heated water through the jacket so that the temperature of the water in jacket 14 is maintained at a temperature that is approximately equal to, or only slightly above the melting point of the organic peroxide to be purified. The sections of conduits 10a and 10b extending from jackets 14 and the short conduit 11 may be enveloped in heat insulating material, as at 17, to prevent the loss of heat therefrom.

As has been previously mentioned herein, the temperature and rate of supply of steam to injectors 12, the rate of transport of suspension by pump 7 through conduits 10a and 10b and the distances along such conduits 10a and 10b and conduit 11 from injectors 12 to the inlet of separator 8 are selected so that the heat transfer from the steam to the suspension is effective to complete the conversion thereof to an emulsion, that is, to fully melt the organic peroxide just prior to the entry of the emulsion into separator 8. In the apparatus shown, the temperature of the emulsion is continuously detected adjacent the inlet to separator 8, as at 18, and such temperature is recorded, as at 19, and employed to actuate a suitable conventional control device 20 which is operative, upon a deviation of the detected temperature from a preset value, to control a valve 21 for regulating the rate of supply of steam to injectors 12 in the sense to restore the preset temperature.

The centrifugal separator 8 is operative to separate the aqueous and liquid peroxide phases of the emulsion admitted through conduit 11, and the aqueous and liquid peroxide phases are separately discharged, as at 22 and 23, respectively. The separated liquid peroxide phase is solidified, as by rapid cooling on a cooling belt 24 or other suitable means, such as, internally chilled, rotating drums, or atomizing and spraying the liquid peroxide into a cool atmosphere.

In practicing the method according to this invention in the above described apparatus, it has been found suitable to provide the conduits 10a and 10b with internal diameters in the range between 1 and 3 cm., to continuously transport the suspension through such conduits at a linear rate or speed in the range between 0.5 and 2 m/sec., and to supply the steam to injectors 12 at a pressure in the range between 2 and 5 atmospheres corresponding to steam temperatures in the range between 120° and 150°C.

The rate at which steam is injected is regulated, as by valve 21 operated by control 20, as described, so that the quantity of heat transferred by the steam to each flow of aqueous suspension is just sufficient to convert the suspension to an emulsion at a temperature a few degrees above the melting point of the organic peroxide to be purified, for example, at a temperature of approximately 55°C. in the case of dilauroyl peroxide. Further, in the case of the last mentioned organic peroxide, the water temperature in each jacket 14 may be maintained at aproximately 60°C., but it is to be understood that the length of each conduit 10a or 10b coiled in the jacket 14 and the rate at which the suspension/emulsion is pumped therethrough are such as to substantially avoid any heat transfer from the water in jacket 14 to the contents of coil 13. Thus, substantially all of the heat for converting the suspension to an emulsion is derived from the injected steam and, if desired, the jacket 14 through which heated water is circulated may be replaced by other insulating means to prevent the loss of heat to the atmosphere.

Through the use of the relatively small diameter conduits 10a and 10b for the continuous transport of the suspension and the continuous conversion of the latter to an emulsion by the injection of steam therein, the times during which the heat-sensitive organic peroxide is held at a high temperature are uniform for all portions thereof and may be conveniently restricted to very short times. The foregoing accounts for the surprising finding that, although steam temperatures in the range between 120° and 150°C. are employed, no significant decomposition of the organic peroxide is encountered. By reason of the intense mixing of the injected steam with the suspension and the injection of the steam in finely divided form, there is a rapid transfer of heat to all parts of the suspension uniformly, so that no portion of the suspension is heated to temperatures in excess of the safe temperatures for heating of the organic peroxides.

Further, the temperature to which the emulsion is heated may be easily and accurately regulated, as described, to avoid an inadequate temperature, which would result in clogging of the apparatus, or an excessive temperature, which would result in an undesirable decomposition of the organic peroxide.

Although the method and apparatus according to this invention make possible the attainment of extremely short contact times of the liquid or molten peroxide phase with the aqueous phase, so as to avoid decomposition of the organic peroxide, purification to an extremely high degree is nevertheless achieved with these short contact times of well under 2 minutes. Such purification may be further improved by adding, to the water introduced at 5 for forming the suspension, certain specific chemical substances, such as, acid or alkali reacting substances (for example, for the removal of fatty acids), emulsifiers or anti-foaming agents. Since the aliphatic diacyl peroxides, when prepared by the existing methods as described above, are obtained in the form of a fine crystalline powder, no difficulty is experienced in producing an aqueous suspension thereof in vessel 1. A further characteristic advantage of the method and apparatus according to the invention, is that the efficient purification of the organic peroxide can be achieved with a considerable saving in washing water as well as time as compared with previously employed purifying treatments.

In a particular, illustrative example of the method according to this invention using the apparatus described above, the conduits 10a and 10b each have a diameter of 2 cm. and the distance from each injector 12 to the inlet of separator 8 is 18 meters measured along the respective conduit 10a or 10b and the conduit 11. The reaction product admitted at 4 to mixing vessel 1 is a lauroyl peroxide containing 0.7 wt.% fatty acid, 1.0 wt.% soaps and 0.1 wt.% unreacted chloride, and rates of supply of such reaction product and of the water at room temperature admitted at 5 are controlled so that the proportion of water to peroxide in the resulting suspension is 4:1, by weight, that is, the suspension contains 20 wt.% of lauroyl peroxide. The pump 7 propels the suspension through each conduit 10a, 10b at a volumetric rate of approximately 1300 liters/hour, that is, at a linear speed of approximately 1.15 M/sec. The steam supplied to each injector 12 is at a pressure of 3 atmospheres absolute, that is, at a temperature of 133°C., and the rate of supply of steam to each injector is approximately 96 Kg/hour. Such supply of steam to each injector in effective to raise the temperature of the suspension in each conduit 10a, 10b to approximately 55°C. and to cause complete melting of the peroxide, that is, to convert the suspension to an emulsion, immediately prior to the discharge thereof into separator 8. The temperature of the water in each jacket 14 is maintained at approximately 60°C. to prevent the loss of heat from each conduit 10a, 10b. After separation of the liquid peroxide from the aqueous phase in separator 8 and the resolidification of the peroxide phase on chilled belt 24, it is found that the resulting purified product contains 99.6 wt.% lauroyl peroxide, 0.18 wt.% water, 0.14 wt.% fatty acid, 0.03 wt.% soaps, and 0.05 wt.% chloride.

Although an illustrative example of the invention is given above, it is apparent that many modifications and changes may be effected therein by one skilled in the art without departing from the scope or spirit of the invention.

What is claimed is:

1. In the method of purifying an impure aliphatic diacyl peroxide which is solid at normal temperature and has a melting point below 120°C. and which has unreacted acid chloride, free fatty acid and/or alkali salts present as impurities therewith, comprising the steps of heating an aqueous suspension of said impure aliphatic diacyl peroxide to a temperature above said melting point for converting said suspension to an aqueous emulsion of the melted peroxide and then separating the resulting aqueous phase containing said impurities and the liquid peroxide phase by means of a centrifugal separator, whereupon the separated peroxide phase consisting essentially of the purified aliphatic diacyl peroxide is solidified by cooling to below said melting point; the improvement of effecting said heating of the aqueous suspension of the impure aliphatic diacyl peroxide by injecting finely divided steam, at a pressure between 2 and 5 atmospheres and a temperature between 120° and 150°C., respectively, into said suspension during its continuous transport, with a linear speed in the range between 0.5 and 2.0m/sec., in at least one path leading to said separator so as to avoid any substantial decomposition of said peroxide therein.

2. The method according to claim 1, in which the time of contact of said aqueous and liquid peroxide phases is limited to less than 2 minutes.

3. The method according to claim 1, in which said suspension is continuously transported to said separator in a plurality of parallel paths and said finely divided steam is injected into the suspension in each of said paths.

4. The method according to claim 1, further comprising preventing the loss of heat from said suspension in said path between the point of injection of the steam and the entry into said separator.

5. In the method of purifying an impure aliphatic diacyl peroxide which is dilauroyl peroxide or dicapryloyl peroxide each being solid at normal temperature and having a melting point below 120°C. and which has unreacted acid chloride, free fatty acid and/or alkali salts present as impurities therewith, comprising the steps of heating an aqueous suspension of said impure aliphatic diacyl peroxide to a temperature above said melting point for converting said suspension to an aqueous emulsion of the melted peroxide and then separating the resulting aqueous phase containing said impurities an the liquid peroxide phase by means of a centrifugal separator, whereupon the separated peroxide phase consisting essentially of the purified aliphatic diacyl peroxide is solidified by cooling to below said melting point; the improvement of effecting said heating of the aqueous suspension of the impure aliphatic diacyl peroxide by injecting finely divided steam, at a pressure between 2 and 5 atmospheres and a temperature between 120° and 150°C., respectively, into said suspension during its continuous transport, with a linear speed in the range between 0.5 and 2.0m/sec., in at least one path leading to said separator so as to avoid any substantial decomposition of said peroxide therein.

* * * * *